United States Patent [19]
Neal

[11] Patent Number: 5,630,792
[45] Date of Patent: May 20, 1997

[54] ANKLE BRACE

[75] Inventor: Charles O. Neal, Knoxville, Tenn.

[73] Assignee: DeRoyal Industries, Inc., Powell, Tenn.

[21] Appl. No.: 568,960

[22] Filed: Dec. 7, 1995

[51] Int. Cl.[6] .................................................. A61F 5/00
[52] U.S. Cl. .......................... 602/27; 602/7; 602/23
[58] Field of Search ................................. 602/5, 6, 7, 23, 602/27–29

[56] References Cited

U.S. PATENT DOCUMENTS

| | | | |
|---|---|---|---|
| 4,517,968 | 5/1985 | Greene et al. | 602/27 |
| 4,587,962 | 5/1986 | Greene et al. | 602/27 |
| 4,693,239 | 9/1987 | Clover, Jr. | 602/27 |
| 4,771,768 | 9/1988 | Crispin | 602/27 X |
| 4,964,402 | 10/1990 | Grim et al. | 602/27 X |
| 5,099,860 | 3/1992 | Amrein | 602/27 X |
| 5,282,483 | 2/1994 | Wang | 602/27 X |
| 5,393,303 | 2/1995 | Shiono | 602/27 |

Primary Examiner—Linda C. Dvorak
Attorney, Agent, or Firm—Paul E. Hodges, P.C.

[57] ABSTRACT

An ankle brace comprising a pair of elongated substantially compliant and substantially inextensible body members designed to reside generally vertically along the opposite sides of the ankle. The body members are connected to one another by a flexible strap that passes beneath the arch of the foot and generally vertically upwardly along opposite sides of the foot where the opposite free ends of the strap are releasably anchored to respective ones of the outer surfaces of the body members. The body members are mirror images of one another and are secured to the ankle as by various strapping. On the outer surface of each body member there is provided a malleable elongated stay which extends between the top and bottom of the body member. This stay is anchored to the body member at spaced apart locations along its length such that bending of the stay effects alteration of the cupping of the body member in the malleolus area thereof.

6 Claims, 4 Drawing Sheets

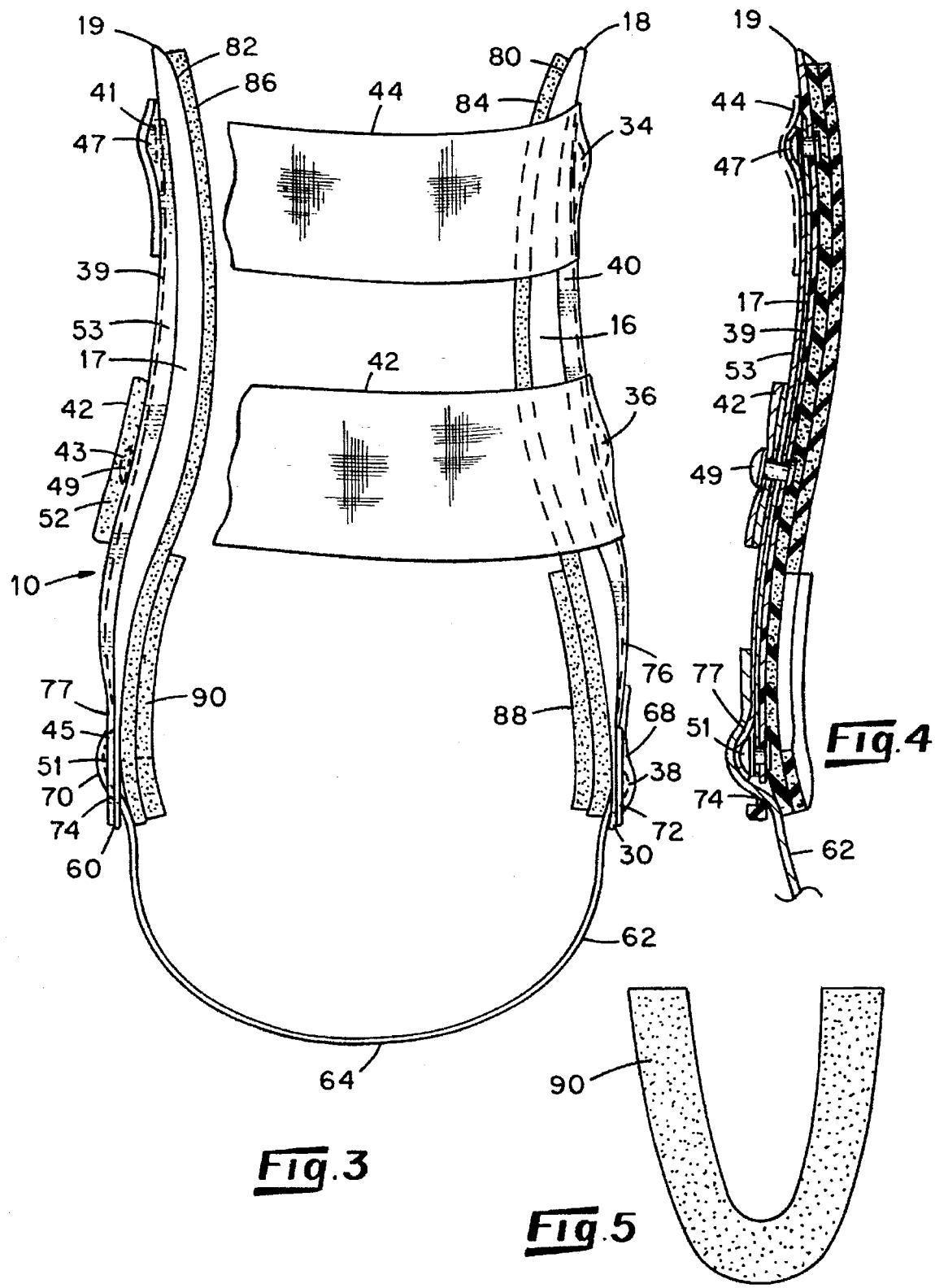

ANKLE BRACE

FIELD OF INVENTION

The present invention relates to ankle braces. The invention particularly relates to an ankle brace which is universal in size, having adjustments in fit, and may be applied to either a left or right foot.

BACKGROUND OF INVENTION

Ankle braces of many kinds exist in the prior art. In general these braces include some form of a body member designed to encircle, partially or completely, a portion of the foot and extending upwardly from the foot about the ankle. Straps, laces and the like have been used to secure the body member to the ankle. Prior ankle braces also include stiffener members, i.e. stays, of various forms.

U.S. Pat. No. 4,237,874 discloses an ankle brace which embodies many of the features of prior art ankle braces in which the body member of the brace wraps a substantial portion of the foot and the ankle. The brace of this patent is secured by lacing and includes a plurality of stays that are held in pockets formed on the outer surface of the body member. This general type of ankle brace is undesirable for many reasons. It is bulky and difficult or impossible to wear with a shoe, its lacing is inconvenient to adjust, and the stays are ineffective.

German Patent No. DE 3909-922-A discloses an ankle brace comprising two rigid shells, one to be fitted to each side of the foot and ankle and held in place against the foot and ankle by elastic straps that encircle the shells in the ankle region. The shells of this brace effectively preclude the use of this brace with a shoe. Further, the shells have no material adjustability as to their fit to the foot and ankle. Still further, the rigid shells are uncomfortable and provide no protection in the area of the lateral and medial malleolus of the ankle. A one-piece elongated rigid plastic body member adapted to pass under the arch of the foot and extend upwardly along opposite sides of the ankle is disclosed in U.S. Pat. No. 4,638,794. The plastic of the body member is softened by heating and molded to the shape of the ankle. Upon cooling, the plastic returns to its rigid condition.

U.S. Pat. No. 5,050,620 discloses an ankle brace comprising a compliant wraparound body member, opening at the front, and which is held in place using hook and loop fasteners. This brace includes a separate strap which is passed under the arch of the foot after the body member is in place and then extended upwardly along the sides of the ankle and anchored to the body member with hook and loop fasteners. This strap is intended to provide adjustable tension to opposite sides of the foot to maintain the foot in a neutral position.

None of the known prior art ankle braces provide for selective protection to the lateral and medial malleolus, but rather they offer body members which, in the region of the malleolus are either compliant, hence nonsupportive, or rigid and therefore nonadjustable as to fit to and over the malleolus. Further, the known prior art ankle braces do not provide for adjustment of the vertical height of the body member of the brace so as to permit selection of the vertical height of the situs of support for the ankle. Neither do they offer to the attending medical practitioner the ability to adjust the fit of the brace to accommodate either the lateral or medial malleolus to thereby provide the maximum support to the ankle without damage or agitation of the malleolus, and simultaneously provide for a single brace to be used on either a left or right foot.

It is therefore an object of the present invention to provide an ankle brace which may be applied to an ankle at a selected vertical height.

It is another object of the present invention to provide an ankle brace which is adjustable by the attending medical practitioner at the time of the application of the brace to an ankle to selectively fit the brace in comfortable and supportive relationship to the lateral and medial malleolus.

It is another object of the present invention to provide an ankle brace which may be applied to either a left or right ankle.

It is another object of the present invention to provide an ankle brace which will accommodate a shoe worn on the same foot to which the brace is applied.

It is another object of the present invention to provide an ankle brace having an improved stay disposed generally vertically along one or both of the sides of the ankle.

It is another object of the present invention to provide a novel system for imparting adjustable rigidity to an ankle brace along the opposite sides of the ankle.

BRIEF DESCRIPTION OF THE DRAWINGS

These and other objects and features of the present invention will be more fully understood or recognized from the following description and claims, including the drawings, in which:

FIG. 3 is a front elevational view of an ankle brace embodying various of the features of the present invention;

FIG. 4 is a sectional view of the ankle brace depicted in FIG. 3 and taken along the line 4—4 of FIG. 3;

FIG. 5 is an front elevational view of one embodiment of a supplementary support pad for fitting about the malleolus of an ankle, and;

SUMMARY OF THE INVENTION

Figure 1:
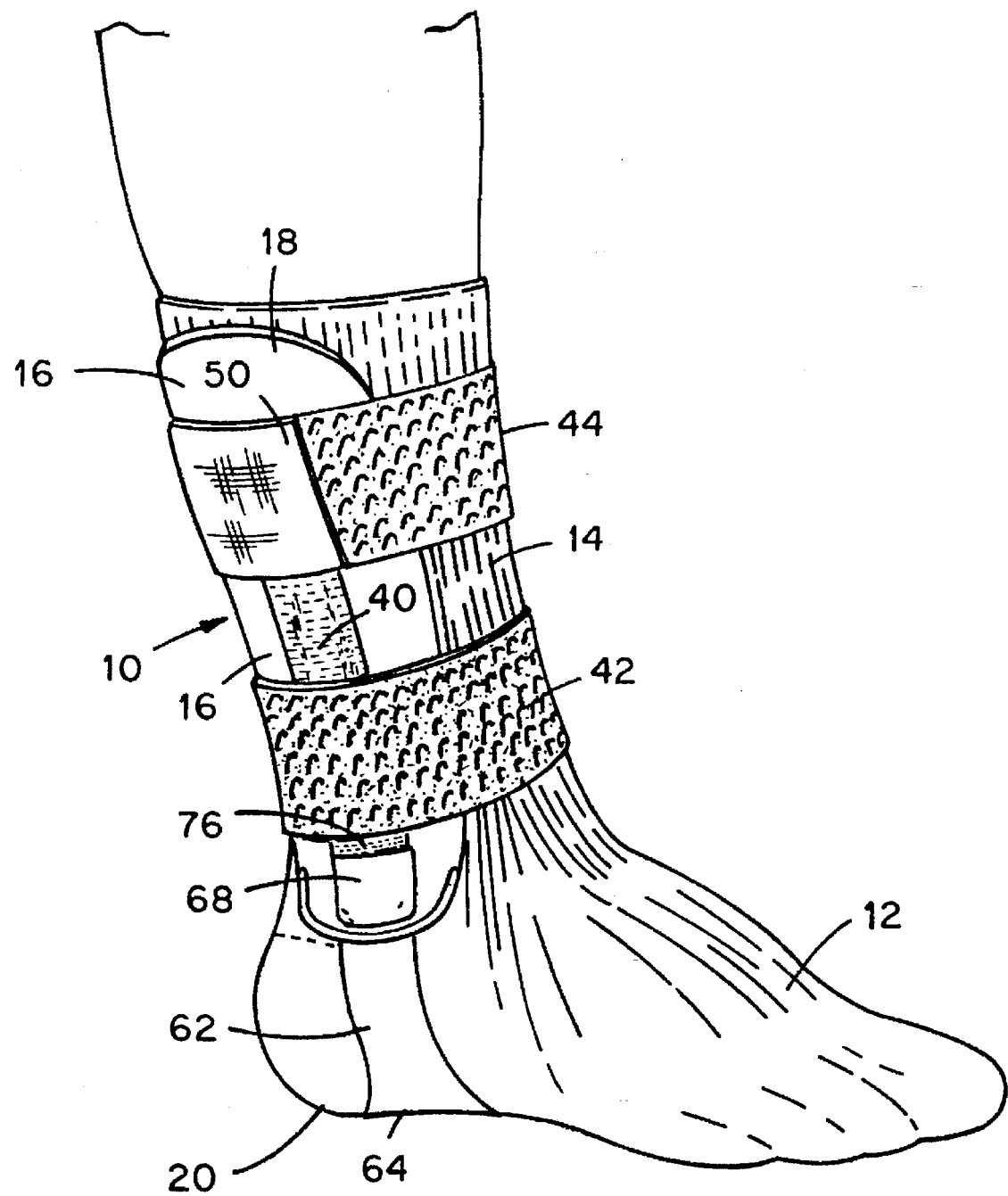
FIG. 1 is a representation of a foot and ankle to which an ankle brace embodying various of the features of the present invention is applied.
Figure 2:
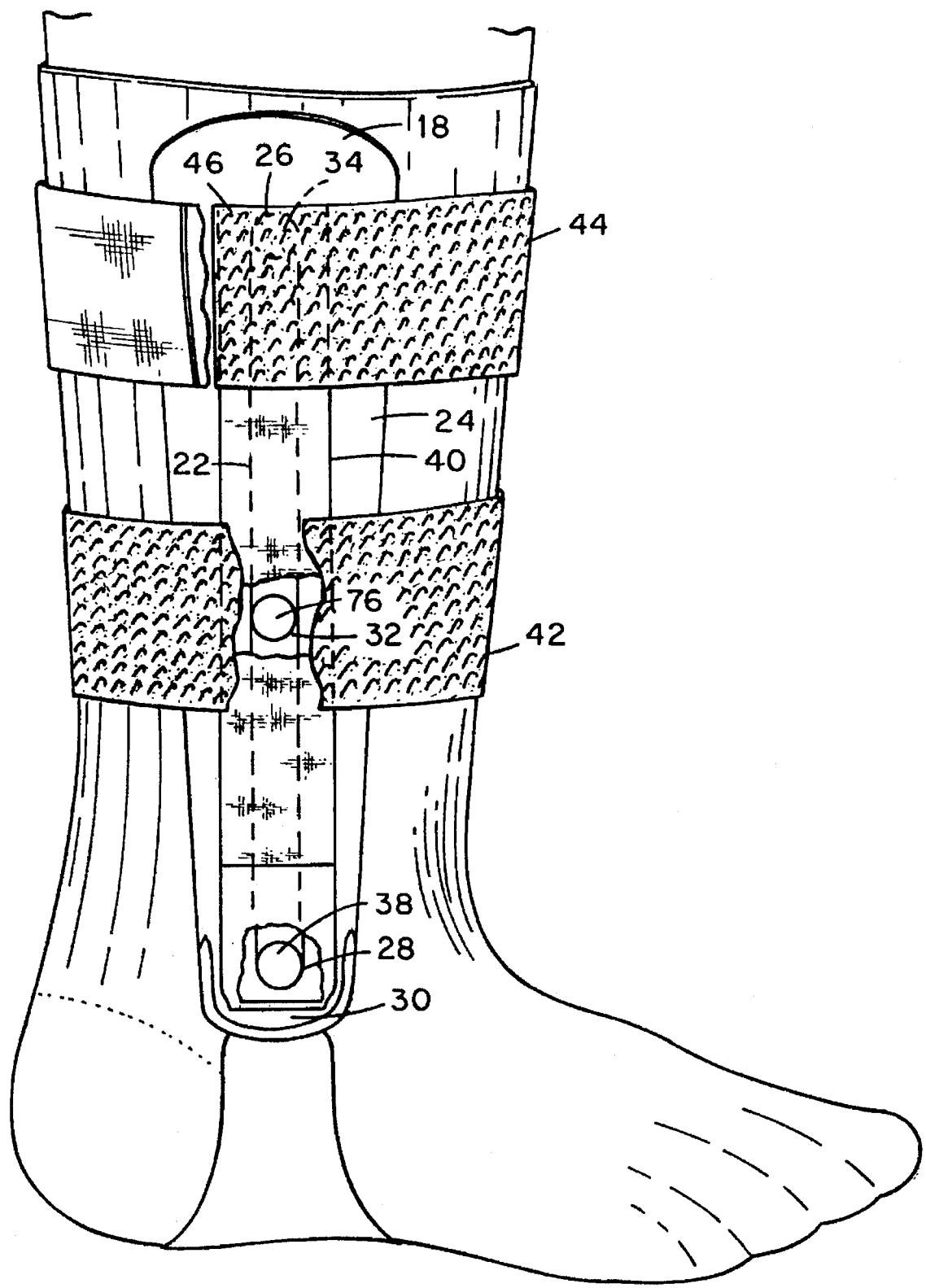
FIG. 2 is a side elevational view of a foot and ankle to which one embodiment of an ankle brace according to the present invention is applied.

In accordance with the present invention there is provided an ankle brace comprising a pair of elongated body members designed to reside generally vertically along the opposite sides of the ankle. The body members are connected to one another by a flexible strap that passes beneath the arch of the foot and generally vertically upwardly along opposite sides of the foot where the opposite ends of the strap are releasably anchored to respective ones of the outer surfaces of the body members thereby permitting the position of each of the body members to be independently adjusted to a desired vertical height above the foot and particularly relative to the lateral and medial malleolus. The body members are secured to the ankle as by means of various strapping and employing hook and loop fasteners or other suitable attachment means.

The body members are mirror images of one another. Each comprises a contoured and substantially compliant, but substantially inextensible, plastic layer that extends the length of the body member. Inwardly of the plastic layer there is provided a layer of soft foam secured to the inner surface of the plastic layer, this foam layer assuming the contour of the plastic layer. On the outer surface of the plastic layer there is provided a malleable elongated, preferably metal, stay which extends from a location near the top end of the plastic layer downwardly along the side of the ankle to a terminus near the bottom end of the plastic layer. Importantly, this stay is anchored to the plastic layer at three physically separated locations only, these being at the top and bottom of the plastic layer, plus a location substantially midway between the ends of the plastic layer. The stay is unattached to the plastic layer in those regions of the stay which are disposed between the locations of its attachment to the plastic layer. A strip of hook material of a hook and loop fastener is overlaid on the stay and secured to the plastic layer as by adhesive. This strip of hook material serves as the anchor position for the various strapping used to secure the body members to the ankle, and for the ends of the strap which passes under the arch of the foot and upwardly along the sides of the foot.

DETAILED DESCRIPTION OF INVENTION

In the several Figures there is depicted one embodiment of the present ankle brace 10 as applied to a foot 12 and ankle 14. The brace 10 includes first and second elongated contoured body members 16 and 17 adapted to overlie respective sides of the ankle from a location below the lateral and medial malleolus upwardly along the opposite sides of the ankle. In one embodiment, the top ends 18 and 19 of the body members 16 and 17 extend to a location about twelve inches above the sole 20 of the foot.

An elongated stay 22 is mounted on the outer surface 24 of the body member 16 by means of attachment of the stay to the body member at three physically separated locations in the depicted embodiment, namely a first location 26 near the top end 18 of the body member, a second location 28 near the bottom end 30 of the body member, and a third location 32 which is substantially midway between the first and second locations. Brads 34, 36 and 38 or like means serve to attach the stay 22 to the body member at the three locations. This stay is overlaid by a strip 40 of hook material of a hook and loop type fastener, the strip being adhesively bonded to the outer surface 24 of the body member 16 and serving as a receptor for a loop element of various hook and loop fastener means as will be apparent hereinafter. Inasmuch as the second body member 17 is essentially a mirror image of the first body member 16, a further stay 39 is attached to the second body member 17 at spaced apart locations 41, 43 and 45 by means of brads 47, 49 and 51. This further stay 39 is also overlaid with a strip 53 of hook material that is adhesively secured to the outer surface of the body member 17.

The brace is held in position by means of straps 42 and 44 which encircle the ankle and/or lower leg. One end 46 of the strap 44 is anchored to the outer surface 24 of the body member 16, preferably by means of the brad 34. Each of the depicted straps is of a substantially inextensible loop material and includes a short strip of hook material attached to its free end. In use, each strap encircles the lower leg or ankle, capturing the body members 16 and 17 between itself and the leg or ankle, wraps back onto itself, and its free end containing the hook material is releasably secured to the loop material of the strap itself. Preferably one strap encircles the leg or ankle in a clockwise direction and the other of the straps encircles the leg or ankle in a counter-clockwise direction. The second strap 42 has one of its ends 52 anchored to the body member 17, as by means of brad 49, and after encircling the leg or ankle and body members, its free end (not shown) wraps back upon the strap and is releasably secured to the loop material of the strap.

The two body members 16 and 17 are connected to one another at their respective bottom ends 30 and 60 by means of a substantially inextensible strap 62 which is of a loop material. The central portion 64 of this strap underlies the arch 66 of the foot 12. The opposite end portions 68 and 70 of the strap extend upwardly from the foot arch along respective ones of the opposite sides of the foot and preferably are fed through open slots 72 and 74 in the bottom ends 30 and 60 of the body members 16 and 17. These free end portions 68 and 70 are releasably secured to the bottom ends 76 and 77 of the hook strips 40 and 53. Because these strips are not permanently attached to the body members, and because the hook strips 40 and 53 extend extensively along the lowermost portion of each body member, the vertical position of each body member may be selected as desired and thereupon the free end portions 68 and 70 of the strap 62 may be secured to their respective hook strips to assist in establishing the maximum height of the body members relative to the sole of the foot 12. The feeding of the free ends of the strap 62 through the elongated slots 72 and 74 in the bottom ends of the body members 16 and 17 serves, among other things, to align the body members over the arch, to permit vertical adjustment of the body member relative to the sole of the foot, and to assist in retention of the bottom ends of the body members in close proximity to the foot.

The body members 16 and 17 are each lined on their respective inner surfaces 80 and 82 with respective layers 84 and 86 of soft foam to provide comfortable padding between the body member and the leg or ankle. Preferably, each liner is dimensionally coextensive with its body member and is adhesively secured to its body member. As desired, additional padding may be provided in the region of the lateral malleolus or the medial malleolus as by means of a horseshoe-shaped soft foam pad 88 and 90 which may be applied to one or both of the foam layers 84 and 86 by adhesive means or the like.

In accordance with one aspect of the present invention, each of the body members 16 and 17 preferably is of a plastic material which is substantially compliant, and is substantially inextensible, but possesses sufficient rigidity as permits it to supply the desired resistance to rotation of the ankle, or lateral or medial flexion of the ankle, when the brace is applied to an ankle in the manner depicted in the Figures and as described herein. Notably, the brace, however, provides for at least limited planar or plantar flexion of the foot, thereby facilitating walking movements of the foot. One suitable plastic is a linear low density polyethylene, such as Dow 2553, available from Dow Chemical. This plastic is capable of being contoured to a desired shape upon heating and holds this contour upon cooling of the plastic. In a preferred embodiment, each body member is concave along its upper portion to readily conform to the rounded contour of a lower leg or the upper portion of an ankle. The lower portion of the body member is also concave, but is further contoured to define an open cup within which a malleolus is received.

A preferred stay is a narrow elongated strip of metal having a substantially rectangular cross-section. In one embodiment of the present invention, each stay is about one-half inch wide, about three sixteenths inch thick and about eight inches long. Because of its inherent stiffness and its limited width, the stay is not deformable by hand in a manner which will alter its cross-sectional geometry. On the other hand, the stay is deformable by hand in a manner which alters the curvature of the stay along its length. Aluminum or aluminum alloys constitute suitable materials from which the stay can be made.

Figure 6:
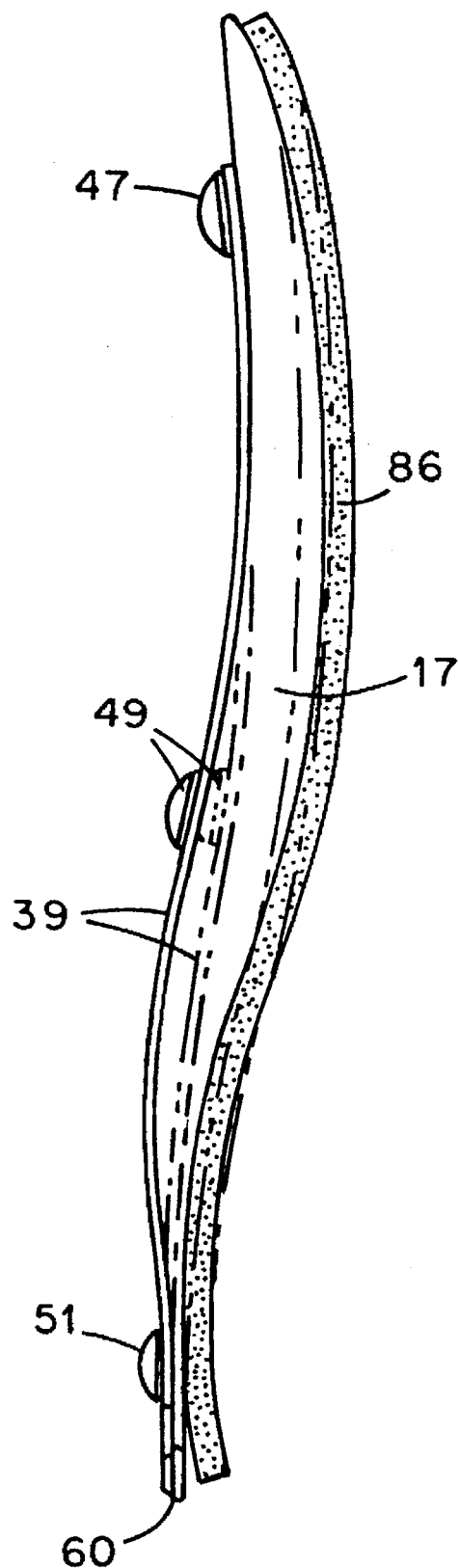
FIG. 6 is a side elevational view of one side member of an ankle brace of the present invention and depicting in dashed lines the flattening of the side member when the stay attached thereto is less bent.

According to one aspect of the present invention, before a stay is attached to its body member, the stay is contoured along its length to substantially match the contour of that portion of the body member to which the stay is attached. This matching contour situation is depicted in FIG. 3. Because the body member is substantially inextensible, once a stay which is contoured to match the convex contour of the body member and is attached to the body member at spaced apart locations, any subsequent bending of the stay in a direction which would tend to straighten the stay is strongly resisted by the inextensible body member. This resistance enhances the strength of the body member to resist movement of the ankle in undesired directions. On the other hand, and referring to FIG. 6, the present inventor has discovered that when the combination of stay and body member is deformed in a manner which tends to increase the bend in the stay, the stay will bend readily because the compliant nature of the body member permits the body member to further cup. In FIG. 6, the relatively cupped geometry of the body member 17, as when the stay 39 is bent, is depicted by the solid lines. The dashed lines are intended to depict a more flat geometry of the body member when the stay 39 is less bent. This action has been found desirable in that it permits a medical attendant to use their hands to bend the stay and enhance the cup contour of the body member to more closely fit the contour of a malleolus which underlies the body member in the cupped region of the body member. Whereas this increased bending of the stay tends to shorten the overall length of the body member, it is to be recalled that the position of the body member is selectable relative to the location of the malleolus because of the vertical adjustability provided for by the strap which connects the body members and passes under the arch of the foot. Accordingly, the body member may be adjusted vertically to ensure that the malleolus is correctly received within the cupped region of the body member. Among other things, this ability to alter the contour of the body member and adjust its vertical height along the leg or ankle permits a body member to be adjusted to properly accept either a lateral or a medial malleolus, even though these be at different vertical heights on the ankle, thereby rendering each body member suitable for use on either side of an ankle and/or on either a right or left ankle.

As noted hereinabove, each stay is attached to its respective body member at spaced apart locations along the length of the body member. By this means, the deformation of the stay for fitting purposes may be performed selectively on the lower half of the body member, for example, where it is most desired. The upper half of the body member commonly needs little or no alteration of the stay after it is attached to the body member, but the adjustability is available if needed. Dividing the stay into two lengths, for example, each of which is independently capable of being recontoured, also has been found to enhance the overall rigidity contributed by the stay to the stay-body member combination.

What is claimed:

1. An ankle brace comprising first and second elongated body members which are contoured to lie along opposite sides of an ankle, each of said first and second body members including
      a layer of substantially compliant and substantially inextensible material having top and bottom ends, an inner surface facing inwardly when the body member is applied to an ankle, and an outer surface facing outwardly when the body member is applied to an ankle,
   and an elongated stay,
      said stay being anchored to said outer surface of said layer at locations near the top and bottom ends of said layer and at a further location approximately midway between the anchored locations near the top and bottom ends of said layer and being unattached to said layer along those portions of the length of said stay that are intermediate said anchored locations, said stay being bendable along its length dimension by hand at least in the region thereof which is unattached to said layer and disposed between its bottom and midpoint anchored locations to said layer to effect recontouring of its respective body member to a cupped geometry at least in the region thereof between the bottom and midpoint anchored locations of said stay to said layer,
   strap means for securing said body members on opposite sides of an ankle,
   further strap means having first and second ends and being suitable to pass beneath the arch of a foot on which the brace is applied and upwardly therefrom along the opposite sides of the foot,
      means releasably anchoring said first and second ends of said further strap means to the outer surface of respective ones of said first and second body members at selectable vertically spaced locations.

2. The ankle brace of claim 1 and including a layer of substantially soft compliant material overlying said inner surface of the body member.

3. The ankle brace of claim 1 and including a pad of soft material secured to the inner surface of one or more of said first and second body members in the region thereof where said one or more of said first and second body members overlies a lateral or medial malleolus.

4. The ankle brace of claim 1 wherein said stay means comprises an elongated metal member having a substantially rectangular cross section and which is deformable by hand in a direction that changes the contour of said stay along its length without materially changing the cross sectional geometry thereof.

5. The ankle brace of claim 1 wherein said stay is contoured along its length prior to its attachment to said layer to substantially conform to the outer surface of said layer onto which said stay is overlaid for attachment thereto.

6. The ankle brace of claim 5 wherein alteration of the contour of said stay along its length effects alteration of the geometry of the cross section of said layer simultaneously with alteration of the contour of said layer along its length.

* * * * *